United States Patent [19]
Orzalesi et al.

[11] 3,973,026
[45] Aug. 3, 1976

[54] INHIBITOR OF BLOOD PLATE AGGREGATION

[75] Inventors: Giovanni Orzalesi; Renato Selleri, both of Florence, Italy

[73] Assignee: Societa Italo-Britannica L. Manetti-H. Roberts & C., Italy

[22] Filed: Feb. 5, 1975

[21] Appl. No.: 547,248

[52] U.S. Cl. ................................. 424/263
[51] Int. Cl.². ........................................ A61K 31/44
[58] Field of Search .............. 424/263; 260/295 AM

[56] References Cited
OTHER PUBLICATIONS

Selleri et al., Chem. Abst., vol. 75, (1971), p. 110153h.

*Primary Examiner*—Sam Rosen
*Attorney, Agent, or Firm*—Cushman, Darby & Cushman

[57] ABSTRACT

There is prepared the compound N,N'-bis-(3-picolyl)-4-methoxy-isophthalamide. It is useful as an inhibitor of blood plate aggregation.

2 Claims, No Drawings

INHIBITOR OF BLOOD PLATE AGGREGATION

The invention relates to an agent inhibiting blood plate aggregation and to a process for its preparation. The inhibitor is a picolyl amide of the 4-methoxy-isophthalic acid and more precisely a compound to which the chemical denomination of N,N'-bis(3-picolyl)-4-methoxy-isophthalamide is applicable.

The compound corresponds to the following structural formula:

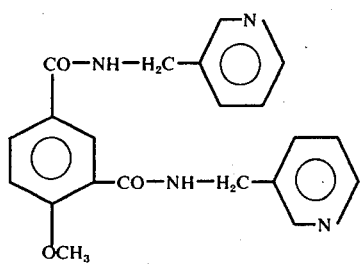

Empirical formula: $C_{21}H_{20}N_4O_3$
Molecular weight: 376.4.

The compound appears as a white, stable crystalline powder, which is easily crystallizable from benzene. Its melting point is 124°C.

For a purely illustrative and in no way limitative purpose, two examples of the preparation of the N,N'-bis(3-picolyl)-4-methoxy-isophthalamide from 4-methoxy-isophthalic acid will now be described.

In these examples, one may operate on the following amounts of reactants:

| | |
|---|---|
| 4-methoxy-isophthalic acid dichloride (molecular weight 233.061) | 0.02 mol 4.7 g |
| 3-aminomethylpyridine (molecular weight 108.146) | 0.044 mol 4.75 g |
| Triethylamine (molecular weight 101.19) | 0.044 mol 4.44 g |

Method A

In a 250 ml three-necked flask equipped with a stirrer, a reflux cooler with a silicon gel guard tube and with a separating funnel, 4.7 g (0.02 mol) of 4-methoxy-isophthalic acid dichloride, dissolved in 50 ml tetrahydrofuran, are placed, thereafter 4.75 g (0.044 mol) of 3-aminomethylpyridine (3-picolylamine) dissolved in 50 ml tetrahydrofuran are added: there is therefore a slight excess of the base with respect to the acid chloride. To the suspension which has formed in the flask, 4.44 g (0.044 mol) triethylamine dissolved in 50 ml tetrahydrofuran are added dropwise through the separating funnel. After this addition has been completed, the mixture is reflux heated for 20 hours under continuous stirring. The excess tetrahydrofuran is distilled under vacuum. The residue is taken up with an excess of a saturated aqueous solution of $NaHCO_3$, it is filtered and the solid residue is washed with water and crystallized from ethanol and recrystallized from benzene. Its melting point is 124°C.

It has been found that N,N'-bis(3-picolyl)-4-methoxy isophthalamide has a marked activity against the aggregation of blood platelets, and is therefore useful in the pharmacological and therapeutical field. This activity has been tested in vitro and in vivo by Born's aggregometer, an apparatus which permits to assess the degree of inhibition exerted upon the tendency of blood plate aggregation.

1. Aggregation inhibiting activity in vitro

Rabbits, which had been kept fasting since 12 hours with water ad libitum, were anesthetized with 20% ethyl urethane, which was injected into them intraperitoneally in the dosage of 0.6 ml/100 g of body weight. Their blood is withdrawn from the carotid artery and taken up with a 3.8% sodium citrate in a 9:1 ratio, and successively centrifuged for 15 minutes at 1000 r.p.m.: a plasma rich in blood plates is obtained, which will be called PRP in the following.

Part of this plasma is centrifuged for 10 additional minutes at 8000 r.p.m., whereby a plasma poor in blood platelets is obtained (to be termed PPP in the following).

The N,N'-bis(3-picolyl)-4-methoxy-isophthalamide, dissolved in 1 N HCl solution (or in a stoichiometric fumaric acid solution) and buffered with phosphates at pH 7.4, is added, at various concentrations, to the PRP in the ratio of 0.1 : 1.0 of plasma, and incubated in a 37°C water bath for 30 minutes. 1.0 ml of the PRP so treated are placed into the cup of Born's aggregometer (zero setting carried out on PPP) and the aggregation of the blood platelets is brought about by a $10^{-2}$ M concentration of the ADP disodium salt.

The activity is computed as the inhibition of the aggregation curve obtained with the same control plasma (incubated in a 37°C water bath for 30 minutes after the addition of 0.1 ml of physiological salt solution per ml of plasma). The value of the control is made equal to 100.

2. Aggregation inhibitory activity in vivo

Rabbits which had been held fasting for 12 hours with water ad libitum, are anesthetized with 20% ethyl urethane which is injected into them intraperitoneally at a dosage of 0.6 ml/100 g of body weight. The blood is withdrawn from the carotid artery, before (control) and after 1 hour and 30 minutes from the intraperitoneal injection of N,N'-bis(3-picolyl)-4-methoxy-isophthalamide at doses of 25, 50, 100 and 200 mg/kg of body weight. The blood samples are taken up with a 3.8% sodium citrate in the ratio 9:1, and thereupon centrifuged at 1000 r.p.m. for 15 minutes.

The aggregation inhibitory activity is assessed with the method already described for the in vitro test, directly upon the various plasmas treated, after their centrifugation.

The confirmation of in vivo inhibitory action of the compound upon the blood plate aggregation has been obtained by injecting intramuscularly the compound into minipigs at a dosage of 20 mg/kg of body weight, as well as treating per os human volunteers with a dosage of 12 mg/kg of body weight, and using the same method of determination.

Results

On the basis of the tests performed on the in vitro inhibitory effect of N,N'-bis(3-picolyl)-4-methoxy-isophthalamide on rabbit plasma, the concentration yielding 50 % inhibition of blood plate aggregation ($IC_{50}$) has been calculated by the probit analysis. It has been found that the molar concentration of the compound capable of inhibiting by 50% the aggregation of blood plates corresponds to $5.2 \cdot 10^{-4}$ M ($IC_{50}$ in vitro).

In the assessment of the aggregation inhibiting effect in vivo in intraperitoneally treated rabbits it has been found that the dosage capable of inhibiting by 50% the aggregation of the blood plates corresponds to 108.2 mg/kg ($IC_{50}$ in vivo).

In the minipigs the activity of the compound reached a maximum of 64.50% in the fourth hour after its injection, while the time limit at which the effect of the compound wore out was 72 hours.

In men a maximum effect of 70.11% was found at the eighth hour after administration, while the time limit within which this effect wore out was also in this case 72 hours.

Acute toxicity of the compound was determined by administering it intraperitoneally to white male Swiss mice. The $LD_{50}$ (FL 95%) tests were performed according to the Litchfield and Wilcoxon method (I. Pharm. exp. Ther., 96, 99 / 1949). A table reporting the results of comparative tests is given below, wherein the compound according to the invention is termed G-137.

|  | G-137 | Aspirin | Heparin | Fluphenamic acid |
|---|---|---|---|---|
| Inhibition of platelet aggregation in vitro | $5.2\ 10^{-4}$M | $9.04\ 10^{-3}$M | — | $3.2\ 10^{-3}$M |
| Anticoagulant activity (recalcification time) | $4.8\ 10^{-3}$M | — | 0.398 U.I./ml | |
| Fibrinolytic activity in vitro | $8.7\ 10^{-3}$M | — | — | $5.7\ 10^{-3}$M |
| Antiinflammatory activity (edema by carragenin) | inactive | 74.5 mg/kg | — | 10.8 mg/kg |
| $DL_{50}$ | 1205 mg/kg | 495 mg/kg | — | 235 mg/kg |

On the basis of these results, and in consideration of its very reduced toxicity, it is expected that this compound will find its field of use in therapeutics, in the form of oral or parenteral preparations, for all those states in which it is advisable to reduce the tendency to spontaneous aggregation of the blood plates, as connected with thrombo- and fibrinophilia.

What is claimed is:

1. A composition effective for inhibition of blood platelet aggregation comprising N,N'-bis(3-picolyl)-4-methoxyisophthalamide dissolved in a liquid vehicle at a molar concentration of $5.2 \times 10^{-4}$ moles.

2. A method of inhibiting blood platelet aggregation comprising administering the composition of claim 1.

* * * * *